United States Patent [19]

Elliott et al.

[11] Patent Number: 4,608,775

[45] Date of Patent: Sep. 2, 1986

[54] MUSHROOM MUTANT STRAINS

[75] Inventors: Timothy J. Elliott, Littlehampton; Michael P. Challen, Midhurst, both of England

[73] Assignee: National Research Development Corporation, London, England

[21] Appl. No.: 634,158

[22] Filed: Jul. 25, 1984

[30] Foreign Application Priority Data

Jul. 29, 1983 [GB] United Kingdom ............... 8320535

[51] Int. Cl.$^4$ ............................................. A01H 15/00
[52] U.S. Cl. ....................................... 47/1 R; 47/1.1; Plt./89
[58] Field of Search .................. 47/58, 1.1, 1; Plt./89

[56] References Cited

PUBLICATIONS

T. J. Elliott and F. A. Langton, "Strain Improvement in the Cultivated Mushroom *Agaricus bisporus*", Euphytica 30, (1981), pp. 175–182.

"Mitteilung en der Versuchsanstalt fuer Pilzanbau der Landwirt Schaftskammer Rheinland Krefeld–Grossheuttenhof", Nov. 6, 1982, pp. 30–46 (English), article by T. J. Elliott.

Primary Examiner—Robert E. Bagwill
Attorney, Agent, or Firm—Murray and Whisenhunt

[57] ABSTRACT

Sensitivity (lack of resistance) to fungicides is a problem in commercial strains of the mushroom *Agaricus bisporus*. Mutant strains, produced from the known parent strains by UV irradiation followed by selection, and having a genetically stable phenotype of insensitivity (resistance) to carboxin or benodanil have now been prepared. These mutant strains give a good yield of fruit in the presence of the fungicide. They have been deposited as patent deposits under the Budapest Treaty at the Commonwealth Mycological Institute.

7 Claims, 4 Drawing Figures

MUSHROOM MUTANT STRAINS

This invention relates to new, fungicide-resistant strains of the mushroom *Agaricus bisporus*.

The fungus *Verticillium fungicola* is pathogenic to mushrooms and is troublesome to control. Certain fungicides, notably carboxin and benodanil, give some control over this pathogen, but these fungicides are phytotoxic to mushroom mycelium. If mushroom strains could be made less sensitive to one of these fungicides, the fungicide could be used to control fungal disease to which they are susceptible.

The mushroom *Agaricus bisporus* is a 2-spored species. That is, it has 2 spores on each basidium. The basidium contains a nucleus formed by fusion of two different but sexually compatible types of nuclei, i.e. carrying different genetic information. Call the nuclear types A and B. The basidium containing the nucleus AB undergoes meiosis to produce 2 spores per basidium. Each spore contains two nuclei and the predominant kind of spore is that containing the different compatible nuclei A and B. These spores therefore give rise to a self-fertile mushroom, since the A and B nuclei in the predominant spores fuse together to give a new nucleus within the basidium. There is therefore, natural in-breeding in *Agaricus bisporus*.

In commerce, it is usual to try to improve strains by selection from multi-spore cultures. This is an empirical approach and one which has not led to a great advance.

A more scientific way of producing strain improvement arises from occasional aberrance from 2 spore production. When occasionally 3 or 4 spores are produced, some of them inevitably contain only one nucleus (since the 4 nuclei produced by meiosis are shared between available spores). The mononucleate spores are not self-fertile: they need to fuse with other mononucleate spores to generate a pair of sexually compatible nuclei in the cells of the mycelium from which a new basidium is formed. Single spore cultures from aberrant basidia are therefore fused in order to generate new strains. The chances of improving the strain for any particular characteristic by this method are very low and, so far as is known, it has not resulted in an improvement in fungicide resistance.

The present invention is based on the mutation of commercially available strains of *Agaricus bisporus*, by irradiation, followed by a selection procedure to give new strains having reduced sensitivity (increased resistance) to carboxin or benodanil. The strains are self-fertile and their fungicide resistance phenotypes are genetically stable. Accordingly, the invention provides these mutant strains, samples of which have been deposited as patent deposits under the Budapest Treaty on the International Recognition of the Deposit of Microorganisms for Patent Purposes at the Commonwealth Mycological Institute, Ferry Lane, Kew, Surrey TW9 3AF, England, on July 9, 1984 under Accession Numbers 287345, 287343, 287344, and 287342. It also includes mutants and variants of each deposited strain.

Full particulars of the deposited mutant strains of the invention are as follows:

| Parent strain from which derived | Deposit number at the CMI | Fungicide resistance phenotype | Sporophore character |
| --- | --- | --- | --- |
| "Somycel 11" | IMI 287345 | Carboxin resistance | Rough cap |
| "Somycel 11" | IMI 287343 | Carboxin resistance | Rough cap |
| "Darlington 649" | IMI 287344 | Carboxin resistance | Smooth cap |
| "Mount White" | IMI 287342 | Benodanil resistance | Smooth cap |

The parent strains from which the mutants are derived are those produced by commercial mushroom spawn makers and in addition are available from the Glasshouse Crops Research Institute (an institute funded by the UK Government through the Agricultural and Food Research Council), Worthing Road, Littlehampton, West Sussex BN17 6LP, England.

The deposit IMI 287345 is the same as the deposit CMI CC 279364 made at the Commonwealth Mycological Institute on 25th July 1983, in connection with the UK Patent Application 8320535 from which priority is claimed, the sample or a sub-culture thereof having been transferred within the collection from U.K. national patent deposit to Budapest Treaty deposit status on 9th July 1984.

Mushrooms are classified according to whether their sporophores have smooth caps (which are usual in the UK) or rough caps. The rough caps have scales and are more off-white in appearance. (The character of the cap is affected by airflow and humidity, i.e. with high airflow and low humidity the amount of scaling increases).

The mushrooms produced by the mutants are of a quality comparable to those produced by their parents.

The invention includes a spawn comprising cereal grains, for example of rye, wheat or millet, and an *Agaricus bisporus* mutant strain of the invention. The formulation can be conventional and can therefore include also gypsum and calcium carbonate to improve flow characteristics and adjust the pH.

The invention is illustrated by the following description of the mutant strain IMI 287345 (previously CMI CC 279364).

The mycelium of the parent strain makes no growth on the medium containing more than 5-10 micrograms/ml of carboxin, i.e., its M.I.C. is 5-10 micrograms/ml. By contrast, the mutant strain IMI 287345 grows in the presence of more than 25 micrograms/ml of carboxin, i.e. its M.I.C. is 25-50 micrograms/ml. It is interesting to note that parent and mutant have a similar $ED_{50}$ for carboxin, $ED_{50}$ being the concentration of fungicide which restricts the radial growth of the mycelium by 50%. For the parent it is about 4 and the mutant about 5 micrograms/ml. Clearly, the mutant is capable of making slow growth at higher concentrations of carboxin than 4 micrograms/ml, whereas the growth of the parent falls to zero very sharply above this concentration.

Merely to find a mutant strain which is carboxin-resistant is not enough. It has to be one which grows well in the absence of carboxin. These two requirements are not very compatible. The mutant strain IMI 287345, however, does have the advantage of growing markedly better than its parent in the absence of carboxin, at the rate of 5.5 mm/day compared with 1.8 mm/day for the parent, as shown by in vitro tests.

The mutant strain is self-fertile, which suggests that it is heteroallelic for mating type, i.e. that the binucleate spores produced following meiosis contain different, compatible nuclei.

The genetic segregation of carboxin resistance of this mutant strain has been tested in the basidiospore progeny of a single spore. The pattern of carboxin-resistant phenotypes was consistent with there being a single dominant gene for carboxin resistance.

The fruiting ability of this mutant strain and its parent has been assessed in the presence and absence of carboxin. The mutant strain has consistently outyielded its parent and has maintained high productivity at concentrations of carboxin which reduce the yield of the parent by 30%.

In a trial of this mutant strain artificially infected with the mushroom pathogen *Verticillium fungicola* there was less disease in the fungicide-treated plots without concomitant loss of yield due to the phytoxicity of carboxin.

The other strains of the invention are generally of a similar character, differing in their cap and in their precise degree and/or kind of fungicide resistance. They have shown good yields of fruit combined with good resistance to the fungicide. Thus IMI 287343 was found to be about 20% more productive than its parent strain and had an $ED_{50}$ for carboxin of 20-25 micrograms/ml. IMI 287344 was about 5% more productive than its parent and had an $ED_{50}$ for carboxin of 5-10 micrograms/ml, and an M.I.C. of 75-100 micrograms/ml, whereas the parent strain had the same $ED_{50}$ but an M.I.C. of 15 micrograms/ml. IMI 287342 also yielded well in trials and had an $ED_{50}$ for benodanil of between 10 and 20 micrograms/ml, and an M.I.C. of 50-75 micrograms/ml, whereas the parent strain had an $ED_{50}$ of less than 5 and an M.I.C. of less than 10 micrograms/ml.

The general method of preparation of the deposited mutant strains comprises mutating the parent strain by UV irradiation, growing colonies of the irradiated strain on a medium containing the fungicide and subjecting the growing colonies to a growth procedure for selecting stable resistance to the fungicide. It must be emphasised, however, that this is not a recipe for quick success. The chances of obtaining a genetically stable fungicide resistant strain by the methods described are low (fewer than 1 in 300,000 of the original hyphal fragments typically survive and show the desired fungicide resistance) 1-2%, and the work is technically difficult. The particular method used is described below, using the induction of carboxin resistance as an example.

The parental strain was grown on complete yeast medium (hereinafter "CYM"), prepared as described below, until the colony fully covered the surface of the plate. Uniform agar plugs were cut from the plates and placed in sterile saline (8.1 g/liter) with a few drops of "Tween 80" as a wetting agent. ("Tween" is a Registered Trade Mark). Plugs and mycelium were macerated using a laboratory homogeniser. Aliquots of the homogenate were subjected to method (a) or (b) below for producing the mutants.

METHOD (a)

The homogenate was plated on solid CYM containing 15 micrograms/ml of carboxin. This concentration of carboxin was used in all carboxin-containing media in this method and in method (b). The plated material was irradiated for 10 seconds using UV light. The UV light used had a wavelength of about 2537 Angstrom units, being the theoretical output of the lamp used.

The irradiated mycelium was incubated at 25° C. for 2-3 weeks. Only about 1% of the material showed growth. Visible mycelial colonies were transferred to a fresh solid CYM containing carboxin. The growing mycelium was then re-plated on solid CYM without fungicide and transferred to fresh solid CYM containing carboxin. This procedure selects only strains in which the carboxin resistance is stable as a result of induced mutation. Material in which the carboxin resistance is the result of physiological adaptation is unselected, as its progeny will not grow on the fresh fungicide medium.

METHOD (b)

The homogenate was plated into empty sterile petri dishes and irradiated for 10 seconds using UV light as in Method (a). The material was the transferred to liquid CYM containing carboxin. Flasks were intermittently shaken to increase aeration. The incubation temperature was 20°-25° C. (room temperature) and the time about 2 weeks. The growing mycelium was transferred to solid CYM containing carboxin. To select for stable carboxin resistance, the same procedure was used as in method (a).

Complete yeast extract (CYM) was prepared by autoclaving the following composition for 20 minutes at 121° C., and 2 atmospheres absolute pressure.

| Ingredients | Grams/liter of distilled water |
|---|---|
| Peptone | 2 |
| Yeast extract | 2 |
| Glucose | 20 |
| Magnesium sulphate (MgSO$_4$.7H$_2$O) | 0.5 |
| Potassium dihydrogen phosphate | 0.46 |
| Dipotassium hydrogen phosphate | 1.0 |
| and, when a solid medium is required: | |
| Agar | 20 |

The invention includes mutant and variant strains, especially those which give rise to stable resistance to the relevant fungicide, and, of course, subject to their giving rise to edible fruit. Preferred mutants and variants of the deposited strains include those conferring improved yield of fruit over the parent strains of the deposited strains, i.e. over "Somycel 11", "Darlington 649" and "Mount White". Mutants can be made by UV-irradiation or by the use of well known chemical mutagens. Variants can be made by breeding, including from aberrant basidia as described above in connection with the prior art.

Figure 1:
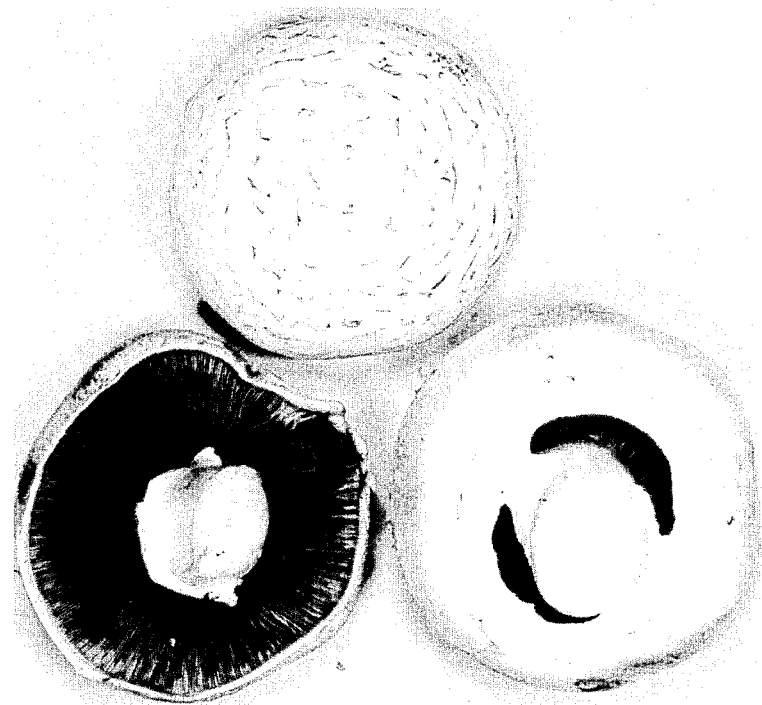
FIGS. 1 to 4 show fruit-bodies of *Agaricus bisporus* strains IMI 287345, 287343, 287344 and 287342 respectively.
Figure 2:
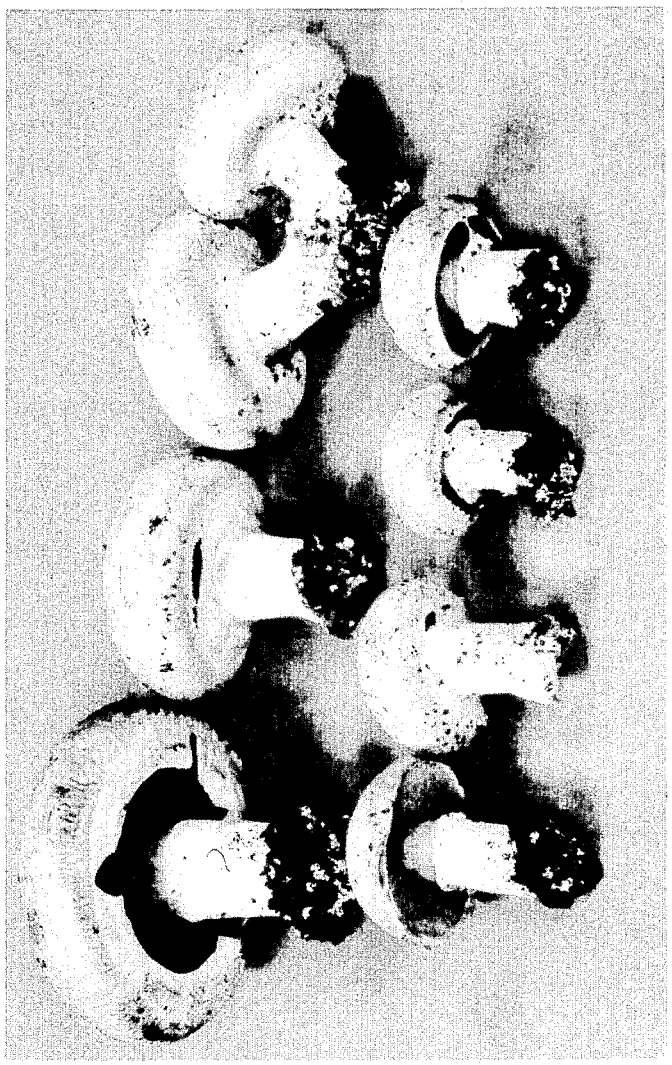
Figure 3:
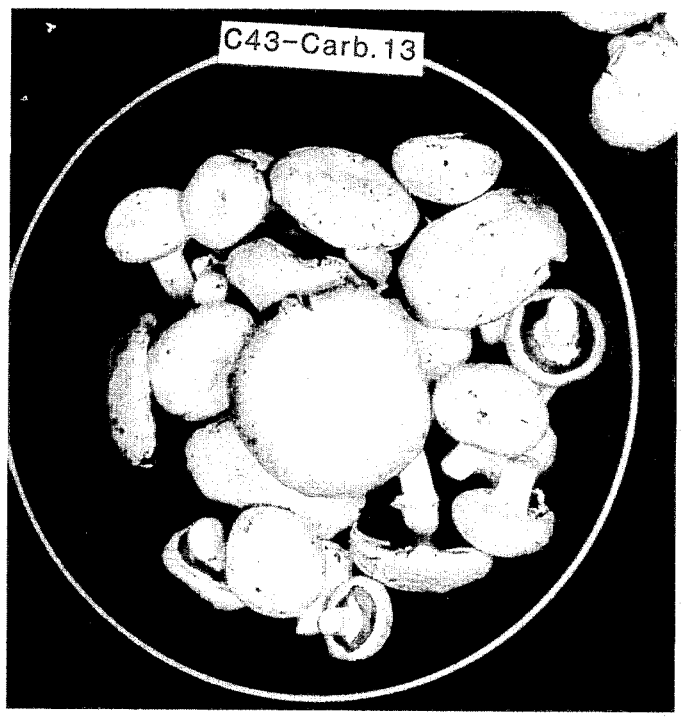
Figure 4:

We claim:

1. A biologically pure culture of a strain of *Agaricus bisporus* selected from the group consisting of the *Agaricus bisporus* strains IMI 287345, 287343, 287344 and 287342 deposited on 9th July 1984 at the Commonwealth Mycological Institute, Ferry Lane, Kew, Surrey TW9 3AF, England, under the provisions of the Budapest Treaty on the International Recognition of the Deposit of Micro-organisms for Patent Purposes.

2. A spawn composition comprising cereal grain and mycelium of an *Agaricus bisporus* strain specified in claim 1.

3. Whole mushrooms derived from a culture of a strain of *Agaricus bisporus* selected from the group consisting of the *Agaricus bisporus* strains IMI 287345, 287343, 287344 and 287342 deposited on 9th July 1984 at the Commonwealth Mycological Institute, Ferry Lane, Kew, Surrey TW9 3AF, England, under the provisions of the Budapest Treaty on the International Recognition of the Deposit of Microorganisms for Patent Purposes.

4. *Agaricus bisporus* strain IMI 287345, deposited on 9th July 1984 at the Commonwealth Mycological Institute, Ferry Lane, Kew, Surrey, TW9 3AS, England, under the provisions of the Budapest Treaty on the International Recognition of the Deposit of Microorganisms for Patent Purposes.

5. *Agaricus bisporus* IMI 287343 deposited on 9th July 1984 at the Commonwealth Mycological Institute, Ferry Lane, Kew, Surrey, TW9 3AS, England, under the provisions of the Budapest Treaty on the International Recognition of the Deposit of Micro-organisms for Patent Purposes.

6. *Agaricus bisporus* strain IMI 287344 deposited on 9th July 1984 at the Commonwealth Mycological Institute, Ferry Lane, Kew, Surrey, TW9 3AS, England, under the provisions of the Budapest Treaty on the International Recognition of the Deposit of Microorganisms for Patent Purposes.

7. *Agaricus bisporus* strain IMI 287342 deposited on 9th July 1984 at the Commonwealth Mycological Institute, Ferry Lane, Kew, Surrey, TW9 3AS, England, under the provisions of the Budapest Treaty on the International Recognition of the Deposit of Microorganisms for Patent Purposes.

* * * * *